US00PP10835P

United States Patent [19]

Zerr

[11] Patent Number: Plant 10,835

[45] Date of Patent: Mar. 23, 1999

[54] POINSETTIA PLANT NAMED 'FISSON MARBLE'

[75] Inventor: Katharina Zerr, Simmern, Germany

[73] Assignee: Florfis AG, Binningen, Switzerland

[21] Appl. No.: 854,674

[22] Filed: May 12, 1997

[51] Int. Cl.[6] ..... A01H 5/00

[52] U.S. Cl. ..... Plt./86.1

[58] Field of Search ..... Plt./86.1, 86.2

[56] References Cited

U.S. PATENT DOCUMENTS

| | | | |
|---|---|---|---|
| P.P. 3,393 | 8/1973 | Ecke, Jr. | Plt./86.1 |
| P.P. 7,799 | 2/1992 | White | Plt./86.1 |
| P.P. 8,833 | 7/1994 | Fruehwirth | Plt./86.1 |
| P.P. 9,365 | 11/1995 | Zerr | Plt./86.4 |
| P.P. 9,819 | 3/1997 | Leighfield | Plt./86.1 |

OTHER PUBLICATIONS

GTITM UPOVROM Citation for 'Fission Marble' As per CAPBR 96–965, Oct. 15, 1996.

*Primary Examiner*—Howard J. Locker
*Assistant Examiner*—Kent L. Bell
*Attorney, Agent, or Firm*—Foley & Lardner

[57] ABSTRACT

A new and distinct cultivar of poinsettia plant named 'Fisson Marble', characterized by its light pink colored bracts with broad white margins, a flat involucre with strongly lobed, medium sized bracts; distinctly lobed intense dark green foliage; compact, bushy and well branched growth habit, medium early flower response, and good post- production keeping quality.

1 Drawing Sheet

The present invention relates to a new and distinct cultivar of poinsettia plant, known by the cultivar name 'Fisson Marble', and botanically known as *Euphorbia pulcherrima*.

'Fisson Marble' is a product of a mutation induction program carried out by the inventor, Katharina Zerr, in Hillscheid, Germany, in 1994.

The primary objective of the induction program was to expand the bract color ranges of 'Fisson', a cultivar disclosed in U.S. Plant Pat. No. 9,365 and characterized by its bright red bracts with pointed lobes, dark green foliage and compact habit.

The irradiation program comprised exposing rooted cuttings taken from plants of the parent cultivar to an X-ray source of 30 Gy dosage in Ahrensburg, Germany, under the supervision of the inventor.

The irradiated plants were grown out in a greenhouse in Hillscheid, Germany, and were asexually propagated by the inventor by taking cuttings. The plants resulting from these cuttings were screened for mutations as small flowering single stem plants in autumn and winter 1994, and the mutations discovered were identified by numbers. Parts of plants showing a positive mutation were left to develop vegetative shoots which were used as cuttings and grown out.

'Fisson Marble' is based on a clone which was derived from a single plant. The clone was discovered in early spring 1995 by the inventor, and had a completely mutated involucre of pink and white variegated bracts.

Subsequent asexual propagation and occasional checking for deviations by the inventor developed a uniform clone with bracts mainly colored pink and with white margins.

The clone (designation No. 139) was examined and compared to other marble colored clones in a trial cultivation in summer 1995 and, on a larger scale, in autumn 1995. This particular clone was chosen because it did not show any leaf deformations at high light intensity, which other variegated clones tend to develop.

Horticultural examination has confirmed that the combination of characteristics disclosed for 'Fisson Marble' are firmly fixed and are retained through successive generations of asexual reproduction.

The following traits have been repeatedly observed and are determined to be basic characteristics of 'Fisson Marble' which in combination distinguish this poinsettia as a new and distinct cultivar:

1. Light pink colored bracts with broad white margins;
2. Flat involucre with strongly lobed, medium sized bracts;
3. Intense dark green foliage, distinctly lobed;
4. Compact, bushy and very well branched growth habit;
5. Medium early flowering response, and
6. Good post-production keeping (or lasting) quality 'Fisson Marble' has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

Of the many commercial cultivars known to the inventor, the most similar in comparison to 'Fisson Marble' are the parent cultivar 'Fisson', and the commercial variety 'Freedom Marble' (U.S. Plant Pat. No. 8,833). The new variety is also similar to 'Fisson White', which is described in copending U.S. plant pat. application Ser. No. 08/854,675 and is similar thereto except for having pink, central bract variegation.

In contrast to the bright red colored parent cultivar 'Fisson', 'Fisson Marble' has pink and white variegated bracts, occasional slightly anthocyanin-colored petioles, and a somewhat taller plant habit. Other morphological characteristics are very similar.

In comparison to 'Freedom Marble', 'Fisson Marble' has smaller bracts with a smooth surface, more intense main pink color which results in a somewhat stronger contrast between the main color of the bract and its margin, and a much more distinctly lobed shape. In addition, 'Fisson Marble' has a later flower response, better cyathia development and retention, and a more compact plant habit.

In comparison to 'Fission White', 'Fission Marble' has white and pink bracks, pink-infused light green leaf petioles, and pink-lined, very light green bract petioles. 'Fission White' has white bracts, light green leaf petioles, and white or slightly greenish bract petioles. 'Fission Marble' has also been repeatedly observed to be slightly taller, about 23 cm, than 'Fission White', about 20 cm.

The accompanying color photographic drawing is a side elevational view showing typical inflorescence and foliage of 'Fisson Marble', with colors being as true as possible with illustrations of this type.

The photograph shows a typical mature potted plant.

The plants described were planted as rooted cuttings in 12 cm pots on Aug. 24, 1995, pinched 14 days later leaving 8 nodes, and were grown at 17°–20° C. minimum day and night temperatures.

The plants initiated flowers under natural short day conditions in autumn. Observations and measurements were mainly taken at the beginning of flowering.

In the following description, color references are made to The Royal Horticultural Society Colour Chart. The bract color values were determined indoors in a north light at temperatures of 17° C.

Classification

*Botanical.—Euphorbia pulcherrima.*

*Commercial.*—Poinsettia, cv. 'Fisson Marble'.

Parentage: Induced mutation of 'Fission'.

*Plant description:*

*Form.*—Shrub, self-branching.

*Growth habit.*—Compact and very well branched; pinched plants are bushy and round shaped; weak to medium growth; Height (above the soil line): 23.0 cm. Diameter/width: 36.0 cm. Average no. of branches: 6.7.

*Stem and color.*—Medium green with slight infusion of anthocyanin in places.

*Rooting.*—Medium, about 20 days.

*Blooming habit.*—The commencement of flowering under natural short day conditions in autumn: Botanially (cyathia open): in early December. Commercially (bracts colored, marketable): around December 1. Flowering response time: about 9.5 weeks.

*Flowering season and keeping quality*—Under winter conditions in Central Europe, commerical quality will be maintained for about 4–6 weeks from date when plant is ready for sale in early December; however, under controlled conditions with sufficient light intensity, the flowering period may be expanded by several weeks; leaf and bract retention is generally better under poor light conditions than that of most varieties with medium green foliage.

*Foliage.*—Shape: Roughly triangular, with acute base, strong pointed lobes, rounded sinus between the lobes, and acuminated tip; smaller leaves without lobes are broad elliptical. Size: Leaf blade: Length: 13.5 cm. Width: 10.0 cm (lobed leaf). Petiole: 5.0 cm. Color: Generally dark green. Upper surface: about 139 A. Under surface: about 137 B. Leaf petiole: Light green, about 147 D, occasional slight infusion of anthocyanin. Texture: Upper surface smooth and flat. Edge of margin: Entire. Leaf and surface and venation: Upper surface: Smooth and flat, only weakly veined with light green,about R.H.S. 146 D. Under surface: Flat and smooth, except for the slightly protruding mibrib and finer side veins, which protrude at an acute, almost right angle from the mibrib; the side veins are evenly spread throughout the leaf blade and run parallel to each other; vein color is light green to greenish white, near R.H.S. 145 B-C.

Flowering description:

*Cyathia.*—In a narrow cluster, few (about 10–14); retention is average when compared to similar cultivrs of this variety; color, light to medium green, with light pink lines; top light pink.

*Bracts.*—Larger bracts are roughly triangular in shape, with acute base, strong pointed lobes, rounded sinus between the lobes, and acuminated tip.

*Bract venation and color.*—The bracts are smooth and flat with veins hardly visible during dehiscence. As bract leaves mature, veins create a more rugose pattern similar to the foliage leaves. Vein color is mainly yellowish-white, about R.H.S. 150 D and the base of the mirib is the same color as the petiole, about 145 C. Mature, fully colored bracts tend to keep their color, fading very little. Bracts that are still growing may become green within about 3 weeks when the plants are exposed to long-day conditions, depending primarily on light intensity.

*Surface.*—Flat or slightly folded, occasionally somewhat rugose.

*Size.*—Largest bract with petiole: 14.0 cm; bract length is about 12.0 cm; petiole length is about 1.8 cm; bract width is about 10.8 cm.

*Color.*—Light pink (may appear slightly marbled) with broad cream-white margin. Upper surface: margin 150 D. Upper surface: main or middle part 50 D for large bracts, 51 C for younger bracts. Lower surface: About 51C-D.

*Petiole.*—Very light green, 145 C, slightly pink lined

*Aspect.*—Horizontal, forming a flat involucre with tips slightly overhanging and center not always closed at the beginning of flowering.

Reproductive organs:

*Nectar cups.*—Small to medium sized, golden yellow in color.

*Stamens.*—Filaments light pink.

*Pollen.*—Yellow, abundant.

*Pistils.*—Style and stigma cream white, 6 lobed stigma.

*Ovaries.*—Light to medium green, triangular, 3 -celled, 3 ovules.

I claim:

1. A new and distinct cultivar of poinsettia plant named 'Fission Marble', as described and illustrated.

* * * * *

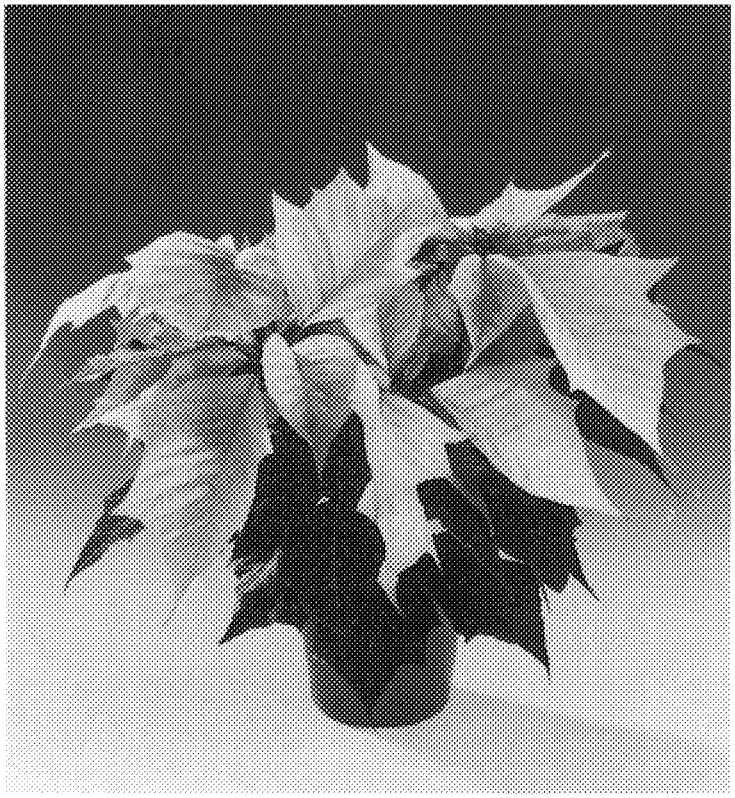

UNITED STATES PATENT AND TRADEMARK OFFICE

CERTIFICATE OF CORRECTION

PATENT NO. : Plant 10, 835
DATED : March 23, 1999
INVENTOR(S) : Katharina ZERR

It is certified that error appears in the above-identified patent and that said Letters Patent is hereby corrected as shown below:

Column 2, line 39, delete "'Fission White', 'Fission Marble'" and insert --'Fisson White', 'Fisson Marble'--. Column 3, line 1, delete "'Fission Marble'" and insert --'Fisson Marble'--. Column 3, line 3, delete "'Fission White'" and insert --'Fisson White'--. Column 4, Claim 1, line 54, delete "'Fission'" and insert --'Fisson'--.

Signed and Sealed this

Seventh Day of September, 1999

*Attest:*

Q. TODD DICKINSON

*Attesting Officer*

*Acting Commissioner of Patents and Trademarks*